(12) United States Patent
Reiner

(10) Patent No.: US 8,117,549 B2
(45) Date of Patent: Feb. 14, 2012

(54) SYSTEM AND METHOD FOR CAPTURING USER ACTIONS WITHIN ELECTRONIC WORKFLOW TEMPLATES

(76) Inventor: Bruce Reiner, Seaford, DE (US)

(*) Notice: Subject to any disclaimer, the term of this patent is extended or adjusted under 35 U.S.C. 154(b) by 271 days.

(21) Appl. No.: 11/586,580

(22) Filed: Oct. 26, 2006

(65) Prior Publication Data

US 2007/0106633 A1 May 10, 2007

Related U.S. Application Data

(60) Provisional application No. 60/730,037, filed on Oct. 26, 2005.

(51) Int. Cl.
*G06F 3/048* (2006.01)
(52) U.S. Cl. ............. 715/751; 705/8; 600/407; 600/437
(58) Field of Classification Search .................. 715/751, 715/738; 705/2, 3, 8; 600/407, 437, 443
See application file for complete search history.

(56) References Cited

U.S. PATENT DOCUMENTS

| | | | | |
|---|---|---|---|---|
| 728,965 | A * | 5/1903 | Pain | 84/111 |
| 5,986,662 | A * | 11/1999 | Argiro et al. | 345/424 |
| 6,458,081 | B1 * | 10/2002 | Matsui et al. | 600/437 |
| 6,574,629 | B1 * | 6/2003 | Cooke, Jr. et al. | 1/1 |
| 6,801,227 | B2 * | 10/2004 | Bocionek et al. | 715/777 |
| 6,904,161 | B1 * | 6/2005 | Becker et al. | 382/128 |
| 6,953,433 | B2 * | 10/2005 | Kerby et al. | 600/443 |
| 7,000,186 | B1 * | 2/2006 | Gropper et al. | 715/202 |
| 7,421,100 | B2 * | 9/2008 | Truyen | 382/128 |
| 7,421,647 | B2 * | 9/2008 | Reiner | 715/230 |
| 7,603,182 | B2 * | 10/2009 | Sano et al. | 700/15 |
| 7,611,452 | B2 * | 11/2009 | Allison et al. | 600/1 |
| 2002/0198454 | A1 * | 12/2002 | Seward et al. | 600/437 |
| 2003/0013951 | A1 * | 1/2003 | Stefanescu et al. | 600/407 |
| 2003/0036925 | A1 * | 2/2003 | Miller | 705/2 |
| 2003/0095150 | A1 * | 5/2003 | Trevino et al. | 345/810 |
| 2003/0204481 | A1 | 10/2003 | Lau | |
| 2004/0002660 | A1 * | 1/2004 | Mielekamp | 600/508 |
| 2004/0054923 | A1 | 3/2004 | Seago et al. | |
| 2004/0122701 | A1 * | 6/2004 | Dahlin et al. | 705/2 |
| 2004/0254465 | A1 * | 12/2004 | Sano et al. | 600/443 |
| 2004/0260593 | A1 * | 12/2004 | Abraham-Fuchs et al. | 705/8 |
| 2005/0021512 | A1 * | 1/2005 | Koenig | 707/3 |
| 2005/0114178 | A1 * | 5/2005 | Krishnamurthy et al. | 705/2 |
| 2005/0168474 | A1 * | 8/2005 | Truyen | 345/581 |
| 2005/0197864 | A1 | 9/2005 | Koritzinsky et al. | |
| 2005/0215867 | A1 * | 9/2005 | Grigsby et al. | 600/300 |
| 2006/0061595 | A1 * | 3/2006 | Goede et al. | 345/619 |
| 2006/0064328 | A1 * | 3/2006 | Datta et al. | 705/3 |
| 2006/0072797 | A1 * | 4/2006 | Weiner et al. | 382/128 |

(Continued)

*Primary Examiner* — Ba Huynh
(74) *Attorney, Agent, or Firm* — Jean C. Edwards; Edwards Neils PLLC

(57) ABSTRACT

The invention provides an electronic workflow method and system that includes a client workstation having a high-resolution image displaying device and an input device, that captures actions that are performed on the image displaying device. The performed actions may include actions that are performed in an interpretation process of medical images displayed by the displaying device. An extensible markup language (XML) schema may be employed to capture and represent the tasks or subtasks. The XML schema records the condensed audit trail of the user actions that are performed during the image review and interpretation process. The invention stores the instructions or actions of the electronic workflow system, although the actions may be stored as an entire "movie" of the electronic workflow system. Thus, the invention dramatically reduces storage, transmission, and time requirements for play back, among providing other benefits.

35 Claims, 5 Drawing Sheets

U.S. PATENT DOCUMENTS

| | | | |
|---|---|---|---|
| 2006/0109500 A1* | 5/2006 | Morita et al. | 358/1.15 |
| 2006/0111937 A1* | 5/2006 | Yarger et al. | 705/2 |
| 2006/0149601 A1* | 7/2006 | Langhofer et al. | 705/3 |
| 2006/0173985 A1* | 8/2006 | Moore | 709/223 |
| 2006/0242143 A1* | 10/2006 | Esham et al. | 707/6 |
| 2006/0285730 A1* | 12/2006 | Habets et al. | 382/128 |
| 2007/0061176 A1* | 3/2007 | Gress et al. | 705/7 |
| 2007/0078678 A1* | 4/2007 | DiSilvestro et al. | 705/2 |

* cited by examiner

SYSTEM AND METHOD FOR CAPTURING USER ACTIONS WITHIN ELECTRONIC WORKFLOW TEMPLATES

CROSS-REFERENCE TO RELATED APPLICATIONS

The present application claims priority from U.S. Patent Provisional Application No. 60/730,037, filed Oct. 26, 2005, the contents of which are herein incorporated by reference in their entirety.

BACKGROUND OF THE INVENTION

1. Field of the Invention

The present invention relates to an electronic image workflow method and system, which includes an electronic auditing function that captures actions that are performed during medical imaging interpretation.

2. Description of the Relevant Art

Over the past decade, a number of technology-driven changes have occurred within the medical imaging field. These changes include the transition from film-based to film-less operation, development of new imaging technologies and applications, (such as multi-detector computed tomography (CT), functional magnetic resonance imaging (MRI), and positron emission tomography (PET)), and widespread adoption of wireless technologies.

Advances in CT and MRI technologies have resulted in dramatic increases in the size and complexity of these imaging datasets, with a single multi-detector CT (MDCT) exam often containing in excess of 1,000 images. The large size and complexity of these imaging datasets creates challenges for both radiologists and clinicians in the various processes of image storage, transmission, display, processing, navigation, interpretation, and reporting.

A clinician, who wants to review a 1,000+ MDCT exam, typically selects either reviewing an entire exam or relies on the radiologist's report. While direct review of the imaging study is preferred in order to directly visualize the abnormalities described and place in the correct clinical context, this is not practical due to time and technology constraints.

One solution includes generating a video file while the radiologist performs the entire process of image display, interpretation, and reporting. While this would provide the clinician with the viewing protocol and findings, it is not practical due to limitations in memory and storage. In particular, resulting video files would be too large for practical storage, transmission, and review.

Thus these and various other drawbacks exist with known systems in the prior art.

SUMMARY OF THE INVENTION

The invention relates to a method and system that captures the "fundamental steps" of an interpretation process. According to one embodiment, the invention provides a method and system for performing an electronic workflow sequence that enables users to selectively review clinically pertinent images, such as a small subset of the entire imaging dataset, in a manner that follows a workflow performed by the interpreting user. The invention enables all users to employ the same image display formats, image processing techniques, and workstation tools for image manipulation. According to one embodiment of the invention, the electronic workflow sequences may be performed on readily available, portable, wireless technologies to overcome any geographic separation between the radiologist and clinician and to enable the invention to be used at various locations.

The invention provides an electronic image workflow method and system, which includes a client computer or workstation with high-resolution image displaying devices, and an input device which is a programmable stylus or other input device, that captures actions that are performed on the image displaying device. According to one embodiment, the actions may be performed using the programmable stylus and/or other input device.

The performed actions, which may include creating symbols, such as checkmarks, dots, or annotations etc., are preselected to signify certain information. The performed actions may utilize an economy of actions that are diverse in nature and have broad based appeal to the population of end users. At the same time, the performed actions may be made applicable to a variety of different specific situations, modalities, pathologies, etc., in order to interpret the electronic imaging workflow system.

According to one embodiment of the invention, an electronic auditing tool may be provided that enables capturing of "fundamental" data that is contained within the electronic workflow sequence. According to one embodiment, the electronic auditing tool may be configured to capture the individual steps that a user performs during a complex process of image interpretation.

According to one embodiment, the navigation process that is performed by the user employing various workstation tools may be captured and used to create a "movie." According to one embodiment, a "movie" represents actions that are performed by the user during the course of image review, analysis, and interpretation of a dataset.

According to one embodiment, an extensible markup language (XML) schema may be employed to capture and represent tasks and subtasks that are performed by the user. The XML schema records the condensed audit trail of the user actions that are performed during the image review and interpretation process. According to one embodiment, instructions of the electronic workflow sequence may be stored rather than the entire continuous "movie" of the electronic workflow sequence. Thus, the invention dramatically reduces storage, transmission, and time requirements for play back, among providing other benefits.

According to one embodiment, users may review the electronic workflow sequence and may skip, fast forward, rewind, and/or perform other actions on any portions of the electronic workflow sequence.

According to one embodiment, computerized intelligence agents may supplement individual user data input to the electronic medical record (EMR). According to one embodiment, the computerized intelligence agents may query, retrieve, and add additional data to the snapshot of the user workflow system.

According to one embodiment, specialized workflow templates may be designed for individual components of image display, navigation, processing, interpretation, reporting/communication, and data extraction.

According to one embodiment, embedded links may be incorporated into the electronic workflow system to provide access to decision support tools, web sites (via specific URL's), and/or other resources. According to one embodiment, embedded links may supplement the informational content being shared. According to one embodiment, the invention may embed decision support tools into the electronic workflow system.

According to one embodiment, electronic auditing of clinicians may be performed to identify the specific data that is most commonly accessed and used by clinicians. According to one embodiment, frequently accessed decision support tools may be automatically inserted into the electronic workflow system. According to one embodiment, infrequently accessed decision support tools may be automatically deleted from the electronic workflow system. According to one embodiment, an intelligent electronic workflow system may be created that is customized to particular user viewing habits.

According to one embodiment, the invention provides a bidirectional electronic workflow system. According to one embodiment, the invention provides improved communication between parties, with the potential to be used as an educational tool as well as a clinical tool to improve diagnostic accuracy and productivity. According to one embodiment, the auditing tool and XML schema may be employed in medico-legal protection by demonstrating what imaging information was reviewed. According to one embodiment, the auditing tool and XML schema may be employed in medico-legal protection to reconstruct the manner in which imaging information was reviewed.

According to one embodiment, the data recorded by the auditing tool may verify what portions of the comprehensive dataset were reviewed, what types of image processing was used, what decision support tools were used in the image review/interpretation process, among other auditing information. According to one embodiment, the XML schema may serve as an adjunct to the formal report and may provide the electronic workflow sequence by recording the image review process. According to one embodiment, the invention provides an effective electronic communication tool.

There has thus been outlined, some features that are consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DETAILED DESCRIPTION OF THE INVENTION

Figure 1:
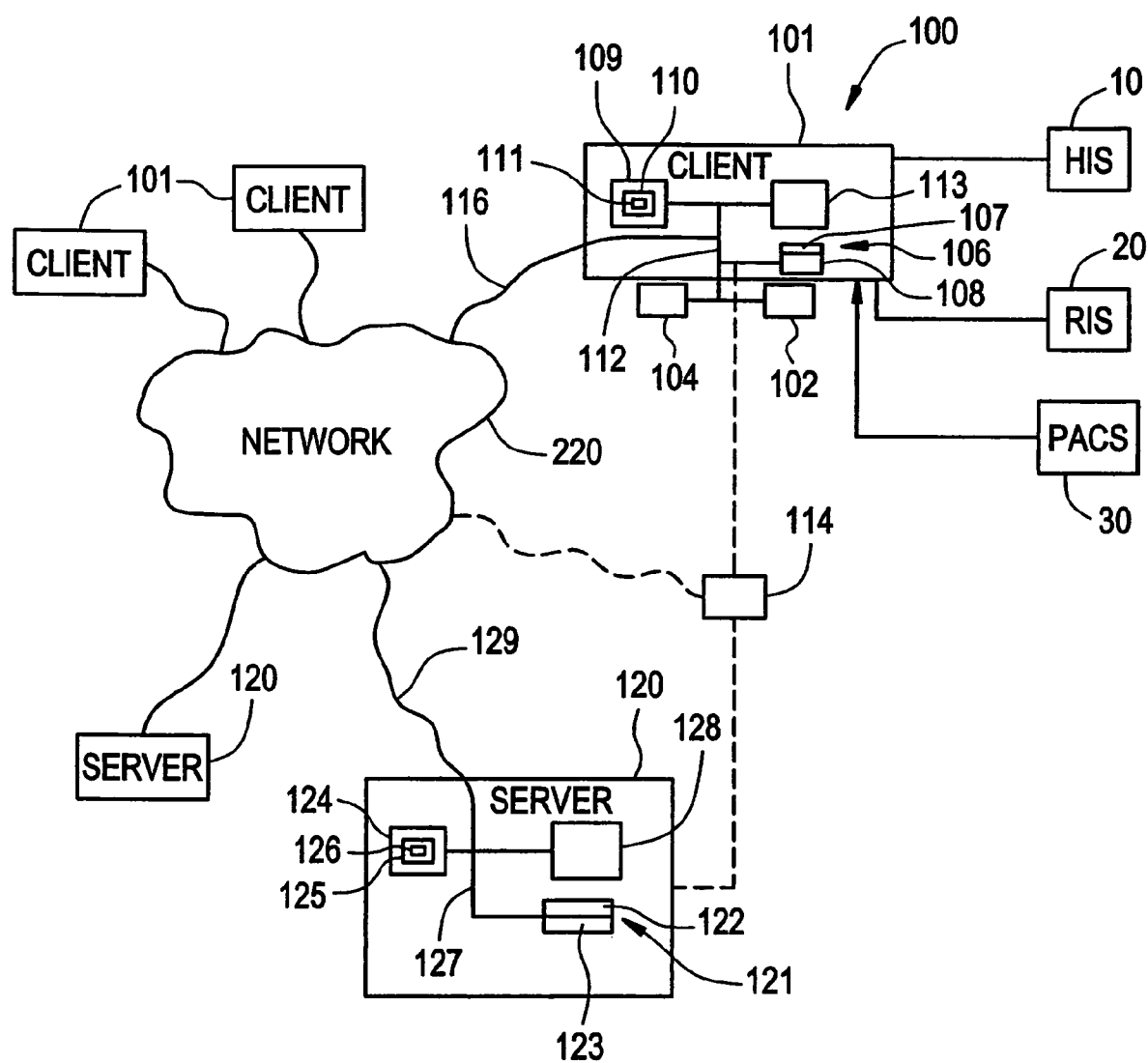
FIG. 1 is a schematic showing the electronic image workflow system according to one embodiment of the invention.

The present invention relates to methods and systems for generating electronic workflow templates that represent user workflow sequences. Applications of this electronic workflow system may be utilized for any type of electronic workflow system that would benefit from presenting captured "fundamental" data that is organized in a workflow sequence to recreate and review the sequence of actions as a multimedia display, that are performed by a user in the fields of medicine (i.e., radiology, endoscopy, surgery, etc.)

The medical (i.e., radiology) application will be the exemplary embodiment as discussed below. In the exemplary radiological application, the present invention includes a computer-implemented method and computer system that function to create a database that includes workflow templates that define electronic workflow systems. The workflow templates may be created using various parameters that define the multi-media display and sequence of actions that are presented to users.

According to one embodiment of the invention, "snapshots" (or captured fundamental data) of user workflow systems provide various user groups with the ability to establish workflow templates, extract context and user-specific data, communicate pertinent clinical and imaging findings, provide interactive educational/training programs, and/or facilitate research, among other functions. From a workflow perspective, workflow templates provide end-users with the ability to follow a pre-designed workflow sequence.

According to one embodiment, workflow templates may include XML schema having specific directions for performing clinical and imaging data extraction, such as image display, navigation, image processing, application of supporting decision support tools, report creation and communication protocols, among other functions. According to one embodiment, end-users may use the workflow templates to effectively review the imaging data in a "hands off" manner. According to one embodiment, end-users may use the workflow XML schema to automatically drive workflow. According to one embodiment, end-users may switch between navigating through workflow systems in an "automatic" and "manual" manner, wherein performing manual navigation includes performing end-user driven tasks. According to one embodiment, the end-users may return to "automatic" workflow navigation mode to re-engage the automatic workflow template navigation and to continue from a selected point within the workflow template navigation sequence, such as the launching point of switching between "automatic" and "manual" navigation.

According to one embodiment, end-users may define workflow sequences and store them as workflow templates. According to one embodiment, the workflow templates may be defined according to various parameters, data sets, target user group, and/or other features. According to one embodiment, the creation of workflow templates includes defining navigation through a workflow sequence as being "automatic" and/or "manual." According to one embodiment, the workflow sequences may be electronically recorded and stored as workflow templates. According to one embodiment, an electronic workflow system is defined by a cumulative sequence of frames that create the workflow templates.

According to one embodiment, the electronic workflow systems may enable re-creation of the exact protocols and data that are captured by the end-users that created the electronic workflow sequence. According to one embodiment, the target end-users may review the electronic workflow system and may modify the electronic workflow system by incorporating additional information, such as unique queries or findings into the exam-specific workflow templates. According to one embodiment, the electronic workflow systems may be modified using XML schema that records the newly introduced user-specific data. According to one embodiment, the target end-user may electronically share the modified workflow templates with the original end-user or end-user that created the electronic workflow sequence. Thus, the invention enables the target end user to share any new observations, questions, or additional clinical data that may not have been available to the original end-user at the time that the original exam review/interpretation was created.

According to one embodiment, the above-described bidirectional functionality of the workflow template provides for continuous clinical dialogue and updating. The bidirectional functionality may transform the imaging exam and the corresponding report into a dynamic, as opposed to static, data source.

According to one embodiment, computerized intelligence agents may also query, retrieve, and/or add additional data to the workflow templates in order to supplement data that is entered to the electronic medical record (EMR) by end-users.

According to one embodiment of the invention, specialized workflow templates may be provided having individual components, such as image display, navigation, processing, interpretation, reporting/communication, data extraction and/or other components. According to one embodiment, data extraction may be performed both before and after exam interpretation. According to one embodiment, the specialized workflow templates may be accessed by end-users, such as radiologists, radiation oncologists, surgical specialists, medical sub-specialists, and/or other end users. According to one embodiment, specialists may include oncologists, pulmonologists, neurosurgeons, orthopedic surgeons, among other specialists. According to one embodiment, the individual specialists may create individual specialized workflow templates, which may be context-specific information, such as based on clinical indication, anatomic region, disease state, imaging modality, among other context-specific information.

According to one embodiment, the dynamic nature of the workflow template provides unique educational and research applications. For example, from an education perspective, the entire workflow process may be reviewed and refined retrospectively to identify "best practice" standards and to teach different user groups. According to one embodiment, these user groups may include technologists, residents in training, clinicians, attending radiologists, among other user groups. According to one embodiment, the user groups may provide customized versions of the workflow templates for educational purposes.

According to one embodiment, the workflow sequences may be stored in extensible markup language (XML) schema to allow for easy accessibility and transportability of complex and data-intensive information. As a result, the workflow templates may be easily modified according to end-user preferences and may be electronically downloaded.

Although the method and system of the present invention are described as being directed to the analysis of digital images, the invention can also be adapted for use with analog images, such as conventional x-ray films, photographs, paper-based images, among other analog images.

According to one embodiment of medical (radiological) system illustrated in FIG. 1, an electronic workflow system 100 of the invention is designed to interface with existing information systems such as a Hospital Information System (HIS) 10, a Radiology Information System (RIS) 20, and a Picture Archiving and Communication System (PACS) 30, among other systems. According to one embodiment of the invention, the system 100 may be configured to conform with the relevant standards, such as the Digital Imaging and Communications in Medicine (DICOM) standard, DICOM Structured Reporting (SR) standard, the Radiological Society of North America's Integrating the Healthcare Enterprise (IHE) initiative, and/or other standards.

According to one embodiment of the invention, bi-directional communications between the electronic workflow system 100 and the information systems, such as the HIS 10, RIS 20, and PACS 30, etc., allows the electronic workflow system 100 to retrieve information from these systems, update information therein and provide the desired workflow templates that are generated by the electronic workflow system 100.

According to one embodiment of the invention, the electronic workflow system 100 may include a client computer 101, such as a PC, which may or may not be interfaced or integrated with the PACS 30. According to one embodiment, the invention includes an imaging display device 102 that is capable of providing high resolution of digital images in 2-D or 3-D, for example. According to another embodiment of the invention, the client computer 101 may include a mobile terminal, such as a mobile computing device, or a mobile data organizer (PDA), that is operated by the user accessing the program remotely from the client computer 101.

According to one embodiment, methods and systems consistent with the invention may be carried out by providing an input mechanism 104 (see FIG. 1), or user selection device, including hot clickable icons etc., or selection buttons, in a menu, dialog box, or a roll-down window of an interface that is provided at the client computer 101. According to one embodiment, commands may be input through a programmable stylus, keyboard, mouse, speech processing system, laser pointer, touch screen, or other input mechanism 104.

According to one embodiment of the invention, the input or selection mechanism 104 may be constituted by a dedicated piece of hardware. Alternatively, the functions of the input or selection mechanism 104 may be executed by code instructions that may be executed on the client processor 106. According to one embodiment, the display unit 102 may display the selection window and a stylus or keyboard for entering a selection, for example.

As described in co-pending U.S. patent application Ser. No. 11/512,199, filed Aug. 30, 2006, which is hereby incorporated by reference in its entirety, a multi-functional programmable navigational stylus 104 may be provided to enable input of gestures, symbols, and/or icons through the imaging display device 102. According to one embodiment, other actions may be performed by the multi-functional programmable navigational stylus 104 that are intrinsic to the image display device 102, such as navigation, interpretation, and electronic workflow processes. The actions performed by the multi-functional programmable navigational stylus 104 on the image display device 102 may be superior to actions that are performed using traditional computer keyboard or mouse methods, both within the PACS and Electronic Medical Report (EMR).

The client computer 101 typically includes a processor 106 that operates as a client data processing device. The processor 106 may include a central processing unit (CPU) 107 or parallel processor and an input/output (I/O) interface 108, a memory 109 with a program 110 having a data structure 111, wherein all of the components are connected by a bus 112. Further, the client computer 101 may include an input device or means 104, a display 102, and may also include one or more secondary storage devices 113. The bus 112 may be internal to the client computer 101 and may include an adapter for receiving a keyboard or input device 104 or may include external connections.

According to one embodiment of the invention, the imaging display device 102 may comprise a high resolution touch screen computer monitor. According to one embodiment of the invention, the imaging display device 102 may be configured to allow images, such as x-rays, to be readable and for the gestures or symbols to be applied easily and accurately. Alternatively, the imaging display device 102 can be other touch sensitive devices including tablet, pocket PC, and plasma screens. The touch screen would be pressure sensitive and responsive to the input of the stylus 104, which may be used to draw the gestures or symbols of the present invention, directly onto the image displaying device 102.

According to one embodiment of the invention, high resolution goggles may be used to provide end users with the ability to review images without the physical constraints of an external computer. For example, a surgeon may wear specialized high resolution goggles to display the cross-sectional radiological image of a brain tumor in 3-D format and may note markings on the image, to highlight the pathology in question and to report pertinent characteristics (i.e., anatomic localization, size, etc.), to serve as a guide during surgery. These goggles may be used for image-guided surgery and gesture-based reporting, for example, such as disclosed in co-pending U.S. patent application Ser. No. 11/176,427, filed Jul. 8, 2005, the contents of which are herein incorporated by reference, and may serve to view images in an electronic workflow system on pertinent findings during the course of surgery.

According to another embodiment of the invention, an internal medicine physician may use these specialized goggles to review images with embedded gestures or symbols, or text. The images could be downloaded using wireless technology and displayed on the goggles, thereby eliminating the need for a computer screen for image display.

According to one embodiment, the graphical user interface associated with the client computer 101 may be a client application that is written to run on existing computer operating systems. According to one embodiment, the client application may be ported to other personal computer (PC) software, personal digital assistants (PDAs), and cell phones, and any other digital device that has a screen or visual component and appropriate storage capability.

The processor 106 at the client computer 101 may be located internal or external thereto, and may execute a program 110 that is configured to include predetermined operations. The processor 106 may access the memory 109 in which may be stored at least one sequence of code instructions comprising the program 110 and the data structure 111 for performing predetermined operations. The memory 109 and program 110 may be located within the client computer 101 or may be located external thereto.

Note that at times the system of the present invention is described as performing certain functions. However, one of ordinary skill in the art will readily appreciate that the program 110 may be performing the function rather than the entity of the system itself.

According to one embodiment of the invention, the program 110 that runs the electronic workflow method and system may include a separate program code for performing a desired operation or may be a plurality of modules that perform sub-operations of an operation, or may be part of a single module of a larger program 110 providing the operation. The modular construction facilitates adding, deleting, updating and/or amending modules therein and/or features within the modules.

According to one embodiment, the processor 106 may be adapted to access and/or execute a plurality of programs 110 that correspond to a plurality of operations. An operation rendered by the program 110 may include, for example, supporting the user interface, performing data mining functions, performing e-mail applications, etc.

According to one embodiment, the data structure 111 may include a plurality of entries, each entry including at least a first storage area that stores the databases or libraries of gesture symbols, or image files, for example.

According to one embodiment, the storage device 113 may store at least one data file, such as image files, text files, data files, audio, video files, etc., in providing a particular operation. According to one embodiment, the data storage device may include, for example, a database, such as a distributed database that is connected via a network, for example. According to one embodiment, the database may be a computer searchable database. According to one embodiment, the database may be a relational database. According to one embodiment, the storage device 113 may be connected to the server 120 and/or the client computer 101, either directly or through a communication network, such as a LAN or WAN. According to one embodiment, an internal storage device 113, or an external storage device 114 is optional, and data may also be received via a network and directly processed.

According to methods and systems consistent with the present invention, the client computer 101 may be connected to other client computers 101 and/or servers 120, including administration, billing or other systems. According to one embodiment, the connections may be provided via a communication link 116 as a client communication means, using a communication end port specified by an address or a port. According to one embodiment, the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

According to one embodiment, the communication link 116 may be an adapter unit capable of executing various communication protocols in order to establish and maintain communication with the server 120, for example. According to one embodiment, the communication link 116 may be constituted by a specialized piece of hardware or may be realized by a general CPU that executes corresponding program instructions. According to one embodiment, the communication link 116 may be at least partially included in the processor 106 to execute corresponding program instructions.

According to one embodiment consistent with the present invention, if a server 120 is used in a non-distributed environment, the server 120 may include a processor 121 having a CPU 122 or parallel processor, which is a server data processing means, and an I/O interface 123. According to one embodiment, the server 120 may be constituted by a distributed CPU 122, including a plurality of individual processors 121 that are located on one or a plurality of machines. According to one embodiment, the processor 121 of the server 120 may be a general data processing unit. According to another embodiment, the processor 121 may include a data processing unit having large resources (i.e., high processing capabilities and a large memory for storing large amounts of data).

According to one embodiment, the server 120 may include a memory 124 with program 125 having a data structure 126, wherein all of the components may be connected by a bus 127. According to one embodiment, the bus 127 or similar connection line may include external connections, if the server 120 is constituted by a distributed system. According to one embodiment, the server processor 121 may have access to a storage device 128 for storing preferably large numbers of programs for providing various operations to the users.

According to one embodiment, the data structure 126 may include a plurality of entries, each entry including at least a first storage area which stores image files, for example. According to an alternative embodiment, the data structure 126 may include other stored information as one of ordinary skill in the art would appreciate.

According to one embodiment, the server 120 may be a single unit. According to an alternative embodiment, the server 120 may be a distributed system of a plurality of servers 120 or data processing units, and may be shared by multiple users in direct or indirect connection to each other. According to one embodiment, the server 120 may execute at least one server program for a desired operation, which may be needed in serving a request from the client computer 101. According to one embodiment, the communication link 129 from the server 120 may be adapted to communicate with a plurality of clients.

According to one embodiment, the invention may be implemented in software that may be provided in a client and server environments. According to one embodiment, the invention may be implemented in software that can be provided in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

According to one embodiment, in a client-server environment, at least one client computer 101 and at least one server 120 are each connected to a network 220 such as a Local Area Network (LAN), Wide Area Network (WAN), and/or the Internet, over communication links 116, 129. Further, even though the systems HIS 10, RIS 20, and PACS 30 (if separate) are shown as directly connected to the client computer 101, it is known that these systems may be connected to the client over a LAN, WAN, and/or the Internet via communication links. According to one embodiment, interaction with users may be through secure and non-secure internet connectivity. Thus, the steps in the methods consistent with the present invention are carried out at the client computer 101 or at the server 120, or at both. According to one embodiment, the server 120 may be accessible by the client computer 101 over for example, the Internet using a browser application or the like.

According to one embodiment, the client computer 101 may communicate via a wireless service connection. According to one embodiment, the server system 120 may communicate with network/security features, via a wireless server, which connects to, for example, voice recognition. However, one of ordinary skill in the art will appreciate that other systems may be included.

In another embodiment consistent with the present invention, the client computer 101 may be a basic system and the server 120 may include all of the components necessary to support the software platform of the invention. Further, the present client-server system may be arranged such that the client computer 101 may operate independently of the server system 120, but that the server system can be optionally connected. In the former situation, additional modules may be connected to the client computer 101. In another embodiment consistent with the present invention, the client computer 101 and server system 120 may be disposed in one system, rather being separated into two systems.

Although the above physical architecture has been described above as client-side or server-side components, one of ordinary skill in the art will readily appreciate that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations may be carried out in hardware, whereas other of the above processing operations may be carried out using software.

The underlying technology allows for replication to various other sites. Each new site may maintain "state" with its neighbors so that in the event of a catastrophic failure, other server systems can continue to keep the application running, and allow the system to load-balance the application geographically as required.

Further, although aspects of one implementation of the invention are described as being stored in memory, one of ordinary skill in the art will appreciate that all or part of the methods and systems consistent with the present invention may be stored on, or read from, other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems consistent with the invention, may contain additional or different components.

Accordingly, in one embodiment consistent with the invention, the electronic workflow system 100 and method as used in an exemplary radiology method and system, includes a client computer 101 with image displaying device 102, and an input device 104, such as a programmable stylus 104 as an input mechanism. According to one embodiment, the programmable stylus 104 may be used to perform other tasks that are intrinsic to the image display, navigation, interpretation, and reporting processes of the invention.

However, although one example described herein is in radiology, one of ordinary skill in the art would recognize that the present invention would be applicable for other medical disciplines, such as navigating through complex datasets, including, for example, endoscopy, cardiology, neurology, and surgery.

According to one embodiment consistent with the present invention, the radiologist may turn on the client computer 101, which may be a stand-alone PC, or connected to a client workstation known in the radiological field as the PACS workstation 30. In this exemplary embodiment, the client computer 101 may be the PACS 30, and some or all of the present invention, with respect to the imaging display device 102, computer memory 109 and program 110 etc., may be contained within the PACS 30 instead of being provided separately. According to one embodiment, the user may log onto the PACS system 30 once the client computer 101 is operational.

According to one embodiment of the invention, the program 110 and/or program 125 may include an electronic auditing function that enables capturing of "fundamental"

data that is part of and contained within the radiologist electronic workflow system 100. According to one embodiment, the electronic auditing function may be configured to capture the individual steps that a radiologist performs during a complex process of medical image interpretation.

Figure 2A:
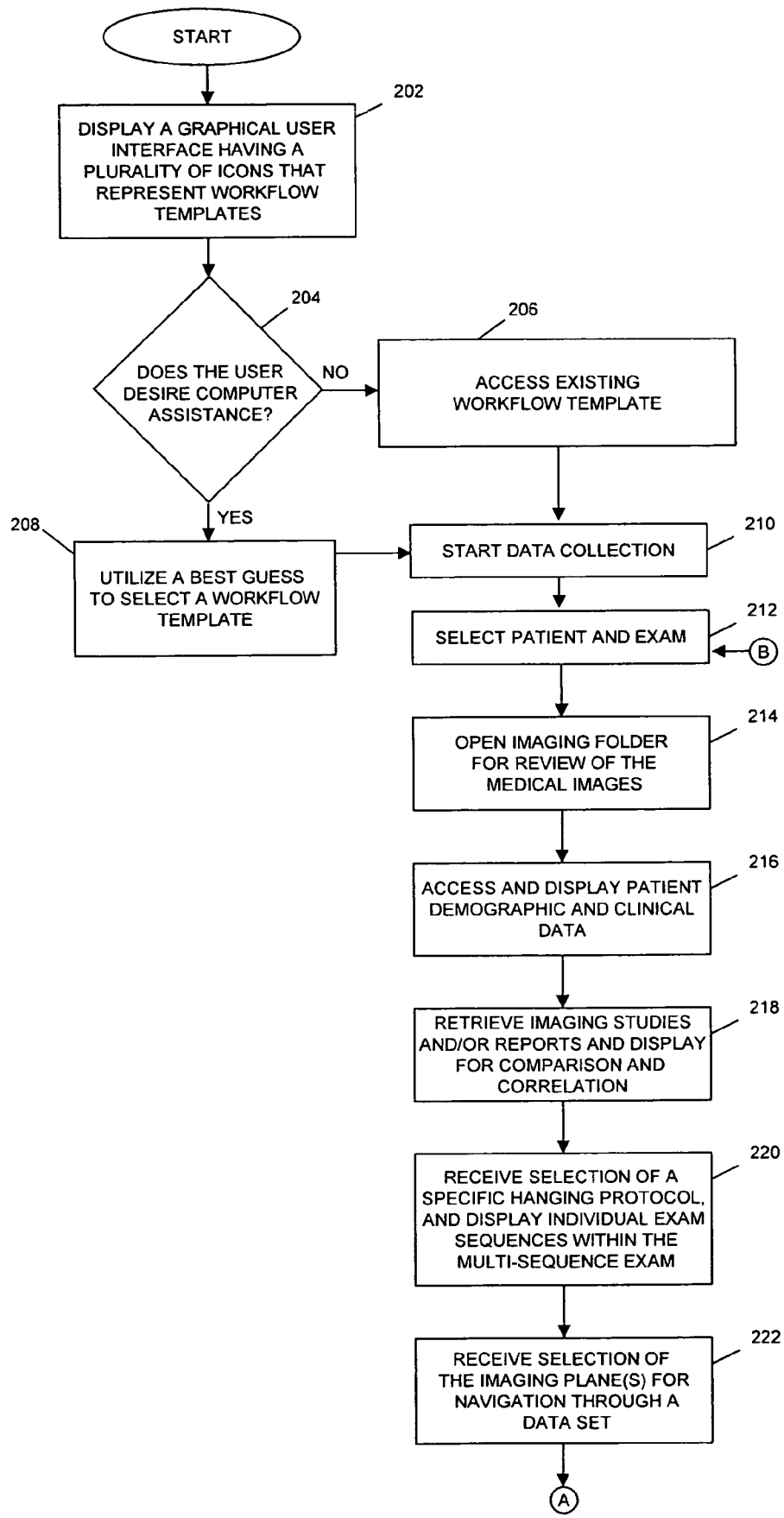
FIGS. 2A and 2B illustrate flowcharts showing the electronic image workflow sequence method according to one embodiment of the invention.
Figure 2B:
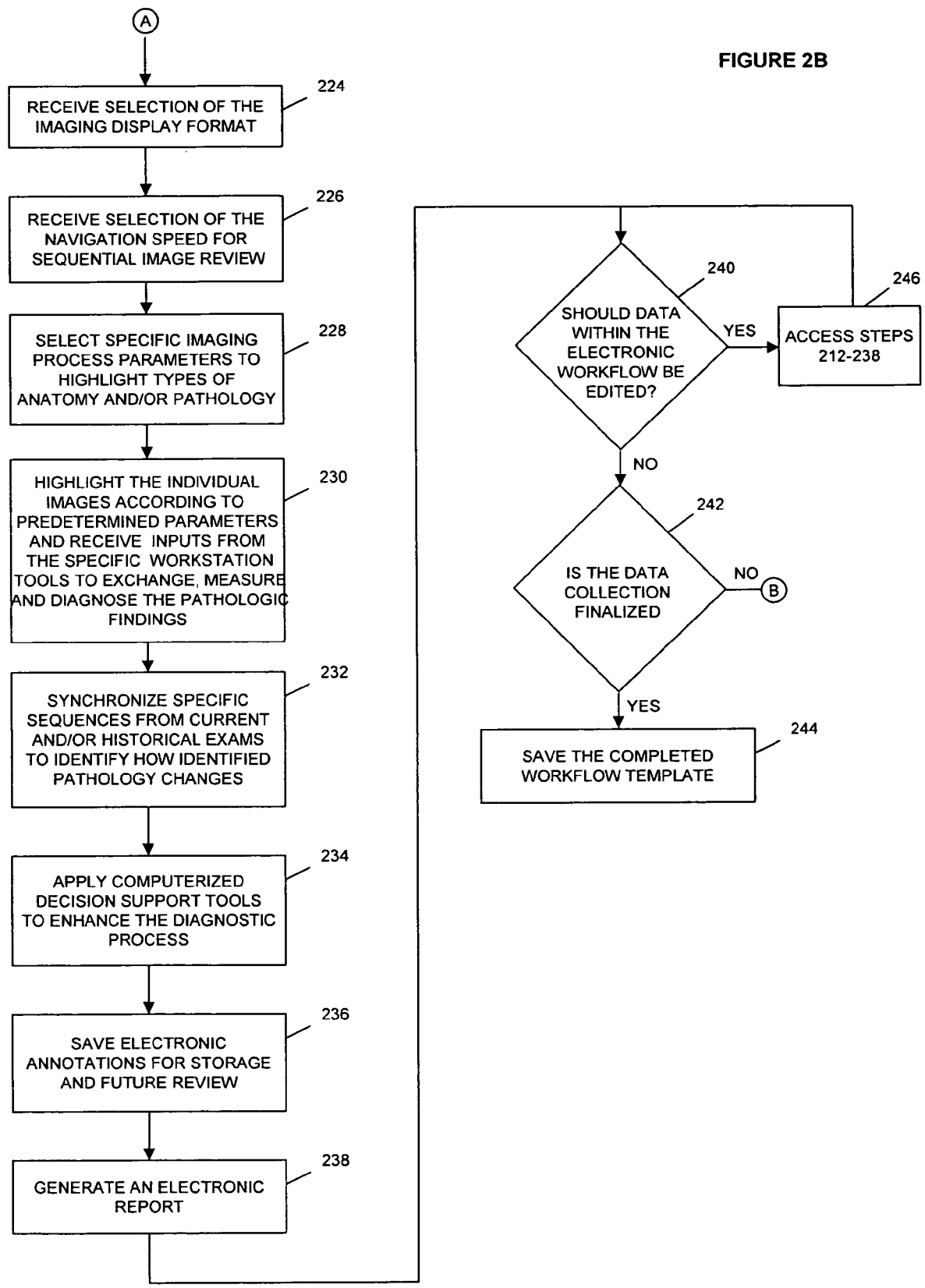

According to one embodiment of the invention illustrated in FIGS. 2A and 2B, once the radiologist or user logs onto the system 100, in a graphical user interface, the program 110 will display a log-on menu that prompts the user to enter unique identifier information, such as a password, biometrics, and/or other unique identifier information. According to one embodiment of the invention, the program 110 may prompt the user to enter additional information, such as patient information, clinical indication, and/or other additional information.

According to one embodiment of the invention, the program 110 may receive the unique identifier information and/or the additional information and may access the storage device 113 having data associated with the unique identifier information and/or the additional information.

According to one embodiment, in step or operation 202, a plurality of icons or menus may be presented to the user based on information retrieved from the storage device 113. In operation 204, the user may be prompted to "access existing workflow templates" or "request assistance from the program 110 to select a workflow template." If the user selects to "access existing workflow templates," then the program 110 will enable the user to select an appropriate workflow template in operation 206.

If the "request assistance from the program 110 to select a workflow template" is selected, then the program 110 will direct the program 110 to utilize a best guess to select a workflow template in operation 208. According to one embodiment, the program 110 may query the EMR based on the unique identifier information and/or the additional information to select the appropriate workflow template.

According to one embodiment, the workflow templates may be customized for each user. According to an alternative embodiment, the program 110 may offer automated default workflow templates without prompting the user. According to one embodiment, the program 110 may select workflow templates based on user profiles. According to one embodiment, the program 110 may adapt workflow template selection to incorporate various parameters.

After a workflow template is selected in operation 208 or accessed in operation 206, the end-user may be prompted by the program 110 to perform a series of actions. Thus, in operation 210, the program 110 will initiate the steps involved in the data collection process. According to one embodiment, auditing software and XML code may be used to record the individual actions that a user performs to generate an electronic workflow template.

In operation 212, the program 110 will receive the input by the user with respect to selection of a patient and an exam that has been conducted. In operation 214, the program 110 will open pertinent imaging folders for user review of the medical images.

In operation 216, the program 110 will access pertinent patient demographics and clinical data from, for example, the hospital/radiology information system (HIS/RIS) and/or electronic medical record (EMR), upon selection of the patient. According to one embodiment, data may be accessed from the PACS 30, and additional information, including but not limited to laboratory data, pathology reports from the Electronic Medical Record (EMR), patient demographics, and billing, may be accessed from data storage 113 by the program 110. According to one embodiment, the PACS 30 may store information in these databases according to existing standards such as DICOM. According to one embodiment, the data from the PACS 30 may be stored in an examination image storage device 114, 128 for example, where it can be accessed via the client computer 101 for display on the image displaying device 102. Alternatively, the electronic workflow system 100 may directly access the PACS images in storage 113 without the need for an intermediate storage device 114 or 128, for example.

In operation 218, pertinent comparison imaging studies and/or reports may be retrieved by the program 110 for correlation with one another, either by overlaying, or by user review. In operation 220, a specific hanging protocol may be selected for displaying individual sequences within the multi-sequence exam. According to one embodiment of the invention, a hanging protocol may be a manner in which a user prefers to arrange a plurality of images for comparison purposes. In other words, a hanging protocol may define a display format for performing a historical comparison study of x-ray information, wherein the comparison is performed for images that are taken over a period of several months.

In operation 222, the relevant imaging plane(s) may be selected for navigation through the data set, by the user, and displayed and/or recorded by the program 110. According to one embodiment, more than one imaging plane may be selected, based on, for example, the modality, anatomy, and pathology being investigated.

In operation 224, the program 110 will display the image in a format selected by the user for use during image review. In operation 226, the program 110 will display the images at a navigational speed selected by the user for sequentially reviewing the images. In operation 228, the program 110 will apply the specific imaging processing parameters selected by the user to highlight certain types of anatomy and/or pathology, on the display. According to one embodiment, displaying specific imaging processing parameters may include the user selecting, and the program 110 displaying, additional applications for the user to access.

In operation 230, as the user identifies pertinent findings, the program 110 will receive notations from the user (i.e., using the stylus 104, for example), and provide highlighting of individual images, and will receive instructions from the user's application of specific workstation tools to enhance (i.e., brightness, size), measure, and diagnose the pathologic findings in question. The tools provide applications such as textual analysis, morphology, density, etc., and are based on user preferences. These preferences can be automated.

In operation 232, the program 110 will synchronize specific sequences from current and/or historical exams to identify how identified pathology changes with different techniques or how identified pathology changes over time. Synchronization is performed by the program 110 linking the same anatomic views, using the same techniques, for example, such that the views are displayed by showing current and previous image studies.

In operation 234, the program 110 will apply computerized decision support tools (e.g., computer-aided detection (CAD)—to mark morphology) as implemented by the user, to enhance the diagnostic process. Computerized decision support tools include functions such as textual analysis, neural networks for differential diagnosis, etc., which can be manually provided, or can be automated.

In operation 236, electronic annotations that are applied (e.g., measurements) by the user, will be received and saved by the program 110 for future review.

In operation 238, the program 110 may generate an electronic report upon request by the user, based on the cumulative findings that are made during the comprehensive image review/interpretation process by the program 110 and the user.

In operation 240, the program 110 may prompt the user regarding whether or not any data within the electronic workflow system should be edited. If any data needs to be edited, then the program 110 may present a menu in operation 246 to enable the user to access any of the data entry user interfaces. If editing is not needed, then the program 110 the user may be prompted by the program 110 requesting whether or not the data collection is finalized in operation 242. In operation 242, the program 110 may perform an audit of the operations conducted above, to determine whether or not any gaps are present, and whether or not data collection is finalized. For example, if the CAD tool used by the user found morphology that was overlooked by the radiologist, the program 110 may notify the user by a warning message box, etc., and may automatically return the display to the image in question.

According to one embodiment, if the data collection is not finalized, then the program 110 will return to operation 212. If the data collection is finalized, then the workflow template is completed and saved by the program 110 in operation 244.

In executing the operations illustrated in FIGS. 2A and 2B, a radiologist may generate in excess of 1000 individual tasks or subtasks with an input device, such as key strokes, mouse clicks, manipulation, programmable stylus, or other input. According to one embodiment, this condensed data may be captured using an electronic auditing function of program 110, which automatically recognizes and records all pertinent tasks or subtasks that are performed by the radiologist or user.

According to one embodiment, the vast data that is produced by the electronic auditing function of program 110 is parsed, organized, and analyzed in a logical and reproducible fashion to provide direct clinical utility by program 110. Direct clinical utility is defined as efficiently capturing a portion of the review process for electronic reporting and consultation for every day clinical use.

According to one embodiment, the navigation process that is performed by the radiologist or user using various workstation tools may be captured and used by the program 110 to create a workflow "movie." According to one embodiment, a workflow "movie" represents actions that are performed by the radiologist or user during the course of image review, analysis, and interpretation of a dataset. Rather than capturing the entire video output of the "movie," the program 110 of the present invention captures each of the separate actions that are performed on the images by the radiologist or user. According to one embodiment, the actions by the user in data collection, for example, may be employed to create each "frame" of the movie. According to one embodiment, the separate actions that are performed by a user and recorded by the program 110 on a given dataset, may be represented in a very tiny fraction (less than 1/1000th) of the size of a file that would be required to capture a continuous video itself, even with the use of compression such as MPEG.

By contrast, producing a continuous video replica of the radiologist review and interpretation process would generate a huge volume of data, which becomes impractical to store and review for consultative purposes. Most clinicians prefer to select and review relevant or "key" images, image enhancements, combinations thereof, and/or images that would be possible in a multiplanar or 3D dataset.

For a conventional 1,000 image MDCT exam, only a small subset of images may have pertinent findings. In other words, the majority of the images may be non-diagnostic images for the clinician. As a result, reviewing the entire dataset may be inefficient, especially for practitioners with limited experience in reviewing images. Furthermore, storage requirements for the entire consultative process, including image display, navigation, processing, interpretation, and reporting, may be impractical. Thus, the present invention provides an abbreviated "workflow" of key imaging data, where an abbreviated "snapshot" of key imaging data may be stored in a "shorthand" format.

According to one embodiment, an XML schema may be employed to capture and represent tasks or subtasks that are performed by the radiologist or user in the data collection. The XML schema records the condensed audit trail of the radiologist or user actions that are performed during the image review and interpretation process.

According to one embodiment, a thick client model, such as a workstation or client computer 101, may be employed to execute the XML schema. According to an alternative embodiment, a thin client model, such as one or more servers 120, may be employed to execute the XML schema. In one embodiment, the audited steps may be recorded by the program 110 at the client computer 101, and in another embodiment, the audited steps may be recorded by the program 110 at the server 120.

Figure 3A:
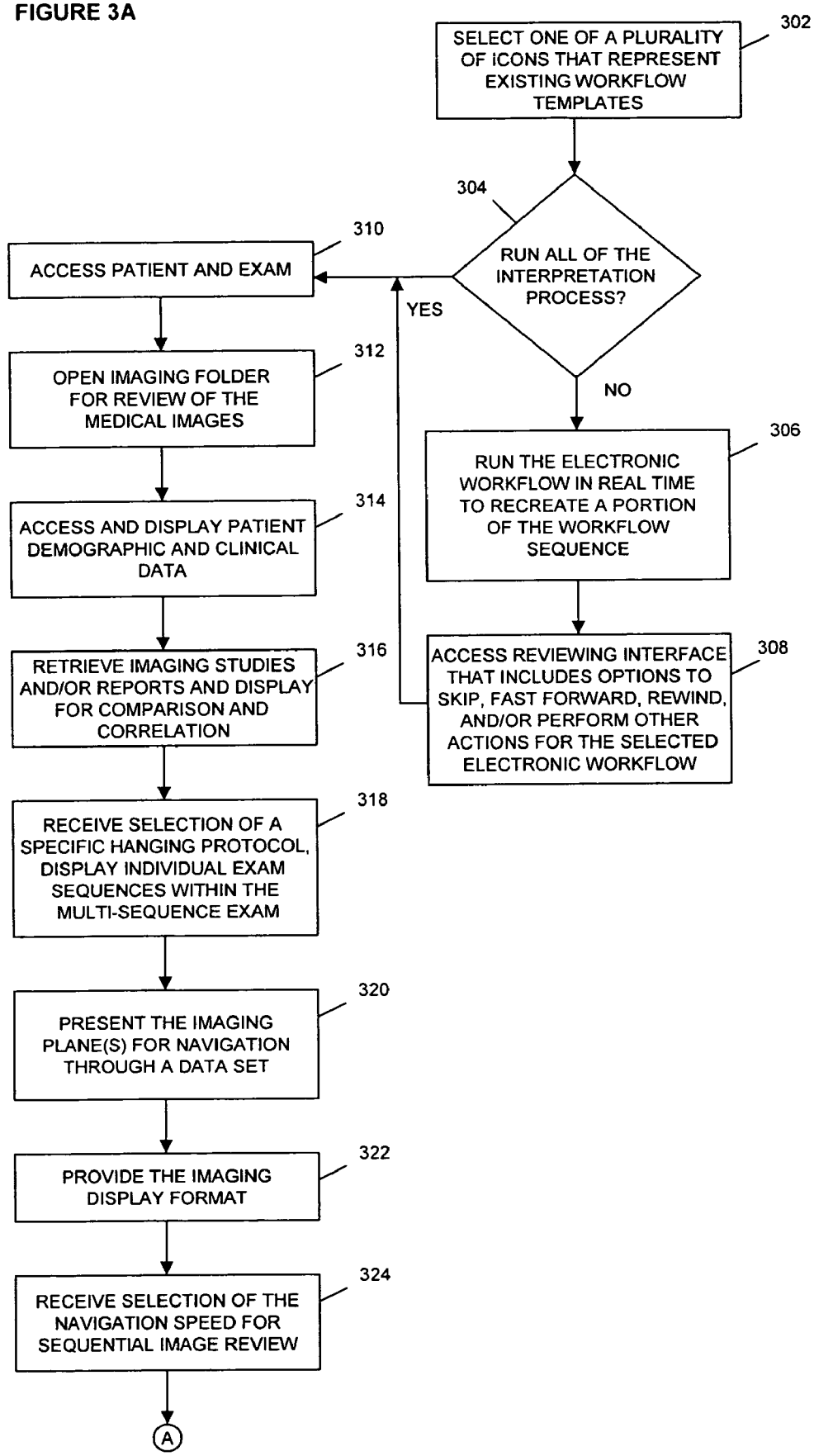
FIGS. 3A and 3B illustrates a flowchart showing the auditing method according to one embodiment of the invention.
Figure 3B:
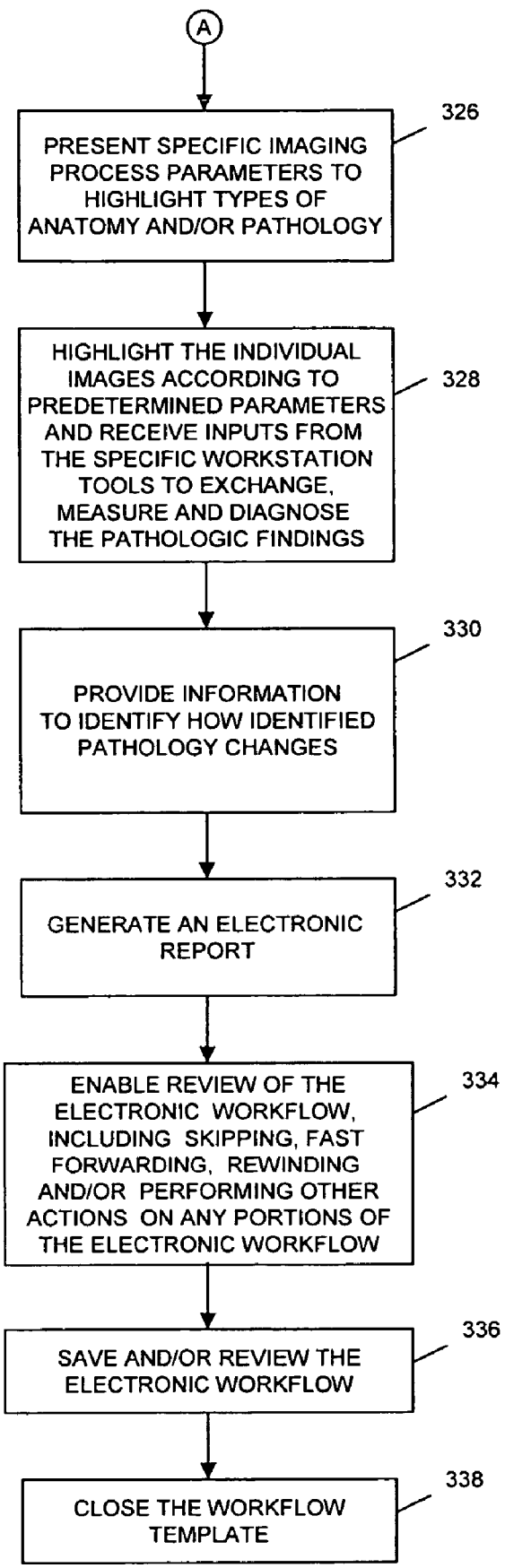

According to another embodiment of the invention illustrated in FIG. 3, a graphical user interface is displayed by the program 110 to target end-users, which can allow the user to review the interpretation process of the electronic workflow system of the present invention utilizing a review interface.

In operation 302, the user is requested by the program 110 to select one of a plurality of icons that represent existing workflow templates. According to one embodiment, the user is prompted by the program 110, in operation 304, regarding whether to recreate all or less than all of the interpretation process. According to one embodiment, if less than all of the interpretation process is to be run, then the user may be directed by the program 110 in operation 306, to a reviewing interface that includes options for the user to return to a particular action, or can skip, fast forward, rewind and/or perform other actions on the selected electronic workflow system in operation 308, similar to that of a DVD remote control.

According to one embodiment, if the entire interpretation process is to be run, then the program 110 may direct the electronic workflow template to the beginning (i.e., operation 206) and may allow the workflow template to be run in real-time to re-create the entire interpretation process (see operations 310 through 332). Reviewing the entire electronic workflow template may include the program 110 displaying the data collection process from operation 206 through operation 244.

According to one embodiment, other users may review, edit, or otherwise modify, and/or save the electronic workflow template in a similar manner as reviewed and/or saved by the original creator/user of the electronic workflow template. For example, individual clinicians may review and/or save an electronic workflow template in a similar manner to how radiologists review and/or save an electronic workflow template. According to one embodiment, the modified session may be saved as a new file, which may be used in conjunction with the original dataset to create a new "movie".

Thus, according to one embodiment, users may review the electronic workflow system and in response to their selections, the program 110 may skip, fast forward, rewind, and/or perform other actions on any portions of the electronic workflow system, in an editing process in operation 334. In operation 336, the revised workflow template may be saved by the program 110. In operation 338, the workflow template may be closed by the program 110

In one example consistent with the operation of the present invention, a brain MRI exam is performed on a patient with documented lung carcinoma and new onset of headaches. According to one embodiment, the brain MRI may be performed with or without contrast using six (6) different imaging sequences performed in axial, coronal, and sagittal planes. According to one embodiment, the results of the brain MRI may be correlated with a previous non-contrast brain MRI performed two years earlier.

According to one embodiment, the radiologist that is interpreting the study may perform the laborious process of linking various sequences from the current study (e.g., axial T1 with and without contrast), in addition to linking current and historical comparable sequences. As the radiologist navigates through the volumetric data set in different planes, a number of enhancing mass lesions are depicted in the cerebellum, right thalamus, and left cerebral cortex. According to one embodiment, in addition to obtaining linear and volumetric measurements of these masses, the radiologist may perform two dimensional (2-D) and three-dimensional (3-D) reconstructions to show the anatomic relationships of these masses to critical structures within the brain, as well as identify the arteries and veins providing blood supply. According to one embodiment, each individual subtask that is performed by the radiologist to obtain those various images and views may be recorded by the program 110 for subsequent playback and editing.

According to one embodiment, an electronic workflow template file is created and may be edited by the user in operations 242 and/or 334, wherein the edits of the image files may be performed using clinician preferences and settings. According to one embodiment, preferences and settings may include slice thickness; image display format; decision support tools, such as segmentation, textual analysis, CAD, temporal subtraction, differential diagnosis; workstation tools, such as magnification, measurements, zoom and scroll; 2-D and 3-D image processing, such as MIP reconstructions, volume rendering, multi-planar reformatting; navigation; synchronization of multiple sequences; compression algorithm; color overlays; annotation of key images; and/or other preferences and settings.

According to one embodiment, each clinician may be provided with or assigned a particular workflow template, which is preset by the radiologist, for example, and stored by the program 110, and which allows each of the clinicians the ability to perform, review, and edit certain functions of the electronic workflow template of the present invention.

For example, a family practitioner may be primarily interested in a summary of pertinent findings. Thus, a "key image" or "key movie" folder may be displayed by the program 110 and when selected by the user, the XML codes recording the radiologist activity for this subset of images may be played back by the program 110.

In another example, an oncologist may prefer a more detailed review of the imaging dataset. Thus, all comparison sequences that link current and historical exams may be included by the program 110 so that the user can determine temporal changes. Since quantitative measurements are critical to the oncology practice, all linear and volumetric measurements may be included by the program 110 in the oncologist review, along with multi-planar reconstructions of the tumors in question. These templates may be customized by or for each user according to their various levels of sophistication and their varying levels of predetermined access to editing.

In yet another example, a neurosurgeon may prefer an extremely detailed review of anatomy in 3-D to simulate the operative field and may request complex 3-D reconstructions with volume rendering from the program 110. This reconstructive data may be included by the program 110 in the neurosurgical electronic workflow template, complete with volumetric measurements and image processing to highlight arterial and venous anatomy. According to another embodiment, the reconstructive data for neurosurgeon review, may be launched by the program 110 by the user accessing the radiologist report or by accessing the images directly.

According to one embodiment, the electronic data may be effectively parsed out by program 110 of the comprehensive auditing data that is collected by the program 110 during the radiologist interpretation process. According to one embodiment, the different data sets for the different practitioners may be created by the program 110 using pre-selected XML codes that are contained within the electronic workflow systems 100. According to one embodiment, the individual XML codes are distinct and separate and may be selected based on user preferences. According to one embodiment, the user preferences may be modified by the user at any time and saved by the program 110. As a result, the program 110 of the present invention enables users to focus reviews on specific subsets of imaging data that is of clinical interest to the end-users.

Thus, according to one embodiment, the program of the client computer 101 and/or server 120 may store the "instructions" (i.e., actions) of the electronic workflow system rather than the entire "movie" of the electronic workflow system. Thus, the present invention dramatically reduces storage, transmission, and time requirements for video play back, as well as providing other benefits to the user.

According to one embodiment, the computerized intelligence agents of the program 110 may supplement individual user data input to the electronic medical record (EMR). The computerized intelligence agents of the program 110 may query, retrieve, and add additional data to the snapshot of user workflow sequences. According to one embodiment, the computerized intelligence agents monitor actions that are performed by users, wherein the actions may be performed using an auditing tool or function. According to one embodiment, the computerized intelligence agents monitor the user actions that direct the client computer 101 to performs steps. According to one embodiment, the computerized intelligent agents learn to perform the user actions, including repetitive actions or other types of actions based on anatomy, clinical indications, patient profile, and/or other criteria. According to one embodiment, the computerized intelligent agents may query EMR to identify actions or other criteria that are associated with the exam and/or patient. According to one embodiment, the computerized intelligent agents may incorporate actions and/or commands into an existing workflow template to created a modified existing workflow template. Alternatively, the computerized intelligent agents may incorporate actions and/or commands into a workflow template to create a new workflow template.

In one example, a radiologist may be tasked with interpretation of a chest CT exam, which may include at least 500 individual images. The clinical indication for the exam may be "lung cancer screening." According to one embodiment, the radiologist may activate a generic workflow template for screening the chest CT. According to one embodiment, the generic workflow template may be an automated workflow template that defines the protocol for data extraction, image display, navigation, interpretation, and reporting. Thus, using this template, the user can effectively review the imaging data in a "hands off" manner, with the electronic workflow system XML schema automatically driving the workflow.

According to one embodiment, the radiologist may elect to convert to a "manual snapshot" status during the image review/interpretation process. According to one embodiment, the "automatic to manual" conversion may be performed electronically through one of many inputs, such as a mouse click on a "manual" icon, a computer keyboard preset button, an electronic stylus, a speech command, or other input. According to one embodiment, the radiologist may convert back to "automatic mode" after performing the desired "manual" tasks.

According to one embodiment, the manual tasks performed by the user may be recorded in XML schema by the program 110, and may be stored as a new exam/user-specific workflow template by the program 110. According to one embodiment, converting back to "automatic mode" may have the program 110 engage the generic workflow template, which returns to the point in the sequence in which the automatic mode was stopped. In operation by the user, the "automatic to manual" and "manual to automatic" conversion may occur several times, based on the preferences of each individual user.

According to one embodiment, the radiologist may highlight a number of significant findings, such as key findings, that are entered into the radiology report and saved by the program 110, such as "pulmonary nodule", before completing the interpretation/reporting process.

According to one embodiment, the key findings may be recorded by the program 110 into the workflow of user workflow sequences by recording all relevant data, including (but not limited to) the individual image number, anatomic location (in 3-dimensions), image processing parameters used, quantitative data (linear/volumetric/density measurements, textual analysis, interval growth), differential diagnosis, and computer-generated malignancy probability, among other information.

According to one embodiment, the radiologist may electronically link ancillary data, which may be extracted from the EMR (e.g., patient past medical history, lab data, bronchoscopy findings) or the Internet (i.e., teaching file images, journal article references, anatomic atlases), in addition to the computer-generated finding-specific data, to the electronic workflow template file. According to one embodiment, any subsequent data that is contained within the EMR and is relevant to a specific finding may be linked by the program 110 back to the original report by the intelligent computer agents. According to one embodiment, notification may be sent by the program 110 to both the authoring radiologist and clinicians that are involved in the care of the selected patient.

Thus, according to one embodiment, if the lung nodule that is detected and reported was scheduled to undergo subsequent bronchoscopic biopsy, key data from the corresponding bronchoscopy and pathology reports may be electronically added to that exam-specific workflow template by the program 110. In addition, according to one embodiment, information may be electronically tagged by the program 110 to denote the author, date and source of "new" information.

According to one embodiment, the radiologist may receive notification of a revised workflow template by the program 110. According to one embodiment, the radiologist may be provided with the specific added and/or revised content of the revision, by the program 110. According to one embodiment, the radiologist may amend the report and the program 110 may save the amendments in memory.

According to one embodiment, any subsequent reviewers of the exam and/or report may access the longitudinal data with the program 110 providing time and author stamps, illustrating the timing and source of data entry. According to one embodiment, the informational content may be automatically retrieved by intelligent agents of the program 110. According to one embodiment, the informational content may be sent by the program 110 to the radiologist based on an automated rule set that may be user-specific and/or context-specific.

According to one embodiment, specialized workflow templates may be designed by the program 110 based on user preferences, for individual components of image display, navigation, processing, interpretation, reporting/communication, and data extraction. According to one embodiment, specialized workflow templates may be created for use by the program 110 based on user preferences, before and after exam interpretation. By contrast, generic workflow templates may be designed by the user for the comprehensive process of image review, interpretation, and reporting.

According to one embodiment, specialized workflow templates may be applicable to higher end users of imaging data including radiologists, radiation oncologists, surgical and medical sub-specialists (e.g., oncologists, pulmonologists, neurosurgeons, orthopedic surgeons). According to one embodiment, an individual specialist may create individualized specialized workflow templates using the program 110, which may be context-specific and may be based on clinical indication, anatomic region, disease state, and imaging modality. According to one embodiment, specialized workflow templates may be implemented by the program 110 and utilized by the user for image display workflows, navigation workflows, image processing workflows, interpretation snapshots, reporting/communication snapshots, data extraction snapshots, among other specialized workflow templates.

According to one embodiment, the data extraction workflow template may serve as an informational template that contains data that is unique to the specific patient, clinical indicator, and imaging exam performed. According to one embodiment, data may be extracted by the program 110 from various informational sources within the medical enterprise including the EMR, PACS, HIS/RIS, among other data sources. According to one embodiment, each individual end user may establish unique preferences and profiles that are integrated into specialized workflow templates by the program 110. According to one embodiment, the specialized workflow templates may include context-specific data.

According to other embodiments, specialized data extraction workflow templates may be provided for a radiologist, a pulmonologist, a family practitioner, and a thoracic surgeon by the program 110.

In one example, the imaging exam being evaluated may be a chest CT that is performed to evaluate a patient with chronic cough and poorly defined right upper lobe density on chest radiography. According to one embodiment, the patent may recently have undergone both bronchoscopy and thoracscopy for diagnosis. In this example, a workflow template for a general radiologist may include both report and imaging data from recent chest imaging exams, such as a recent chest radiograph and a prior chest CT performed one year earlier. In addition, pertinent data from the patient's medical history, which is contained in the most recent hospital discharge summary, may be queried by the user so that the program 110 may identify any underlying risk factors that might predispose the patient to chest malignancy. According to one embodiment, any previous pathology reports or pertinent laboratory data also may be recorded by the program 110 in the general radiologist workflow template.

According to one embodiment, a workflow template for a pulmonologist may incorporate additional clinical data that may not be contained within the radiologist workflow template based on user-specific preferences. According to one embodiment, a more detailed clinical data profile may be integrated into the pulmonologist workflow template, by the program 110. According to one embodiment, the more detailed clinical data profile may include pulmonary function studies, genetic profiles, bronchoscopy images and report data. According to one embodiment, genetic testing on this patient may reveal an abnormality which may lead to an automated query of the Internet or other research tool by the program 110. For example, two national human genome websites, may be queried by the program 110. According to one embodiment, the automated query by the program 110 may result in the program 110 notifying the user of links to related articles on molecular pharmacology and tumor biomarkers.

In another example, a workflow template for a family practitioner may contain extracted data from recent progress notes, consultants' reports, as well as links to articles. According to one embodiment, the patient's laboratory data may reveal an abnormally low sodium level. When the computer neural network of the program 110 combines this low sodium with the possibility of lung mass (based on the recent chest radiograph report), the differential diagnosis by the program 110 may include SIADH (Syndrome of inappropriate ADH secretion). According to one embodiment, the computer intelligent agents of the program 110 may search pre-selected Internet sites for pertinent review articles on SIADH, including the national medical websites, for example. According to one embodiment, the computer intelligent agents of the program 110 may create links in the family practice workflow template to pertinent articles for user review.

In another example, a workflow template for a thoracic surgeon may contain key imaging, clinical, and pathologic data from previous operative notes in addition to the patient's previous thoracoscopy. In the thoracoscopy report, a note by a user may have been made of early signs of chest wall invasion, with the pathologic report citing bronchogenic carcinoma. According to one embodiment, a review of the surgical options and the relevant case reports may reveal journals that were retrieved from pre-selected medical websites. According to one embodiment, the computer intelligent agents of the program 110 may create links to articles that are integrated into the thoracic surgeon workflow template.

According to one embodiment, based on the user and context-specific data that is integrated into the thoracic surgeon data extraction workflow template by the program 110, the thoracic surgeon image display workflow template may be modified. According to one embodiment, the user may modify the workflow template. According to an alternative embodiment, the program 110 may modify the workflow template.

According to one embodiment, the user can manually perform additional actions and then may prompt the workflow template to incorporate changes into an existing workflow template. According to one embodiment, the modified workflow template may be saved as a new workflow template or as a modified workflow template. According to one embodiment, the program 110 may recognize the manual changes using, for example, electronic auditing tools and then may create a new workflow template that is associated with the user. According to one embodiment, the new workflow template may be generated based on a defined set of descriptors, including a patient clinical profile, ancillary data, clinical indication, imaging modality/anatomic region, image acquisition and/or processing parameters, among other descriptors. In either case, whether performed by the user or the program 110, the end result is a set of user and context-specific workflow templates that may be automatically transported and engaged whenever a user signs into a computer to access medical imaging datasets.

According to one embodiment, thoracoscopy data that reports chest wall invasion may trigger modifications to the image display workflow template, calling for additional 3-D multi-planar reconstructions to be performed. According to one embodiment, data within one specialized workflow template may have an interaction effect on data within another workflow template.

According to one embodiment, program 110 may alternate between displaying generic workflow templates and specialized workflow templates. To perform this function, a user makes assumptions regarding an anticipated target end-user. For example, the user may anticipate that the target end-user is a family practice physician that desires to access an imaging study (e.g. Brain MRI) on a patient with the clinical indication of "seizures."

According to one embodiment, the generic workflow template is created for a family practice physician user group. According to one embodiment, the generic workflow template may be created based on a combined intuition of the user establishing the original templates (e.g. neuroradiologist), a family practice physician user group profile, and the statistical analysis of the auditing tool taken from a subset of family practitioners. According to one embodiment, the anticipated target end user, such as a member of the family practitioner user group, may review the brain MRI using the generic workflow template. According to one embodiment, the anticipated target end user may manually perform additional actions while viewing the images. The additional actions may not be defined within this generic workflow template. According to one embodiment, the program 110 may recognize the additional actions and may query the targeted end-user on whether or not the additional actions should be stored to a modified workflow template or a specialized workflow template for Brain MRI/Seizures. If the targeted end-user responds affirmatively, then the program 110 creates a new specialized workflow template that is unique to the end-user, the modality (MRI), the anatomic region (Brain), and the clinical indication (Seizure).

According to one embodiment, the target end-user may find an abnormality in the imaging study (i.e. area of pathology) during the image review that warrants further investigation. During one imaging sequence (e.g. axial T2 spin echo sequence), an area of increased signal intensity may be identified relative to the surrounding brain. The target end user may be unsure of the underlying pathology and exact anatomic location. The target end user may manipulate program 110 to initiate a decision support tool that will attempt to define the anatomic region (e.g., hippocampus) and the specific type of imaging characteristics using data from the additional imaging sequences performed. According to one embodiment, the target end user may utilize a computerized differential diagnosis program to identify the potential types of pathology causing this signal abnormality. The program 110 may identify and list, for example, mesial temporal sclerosis as the principle differential diagnostic entity of concern.

According to one embodiment, the program 110 may perform a search to identify a specialized workflow template for that pathologic entity (i.e. mesial temporal sclerosis), which is utilized by another end-user (e.g., neurologist). The program 110 may query the target end-user regarding whether or not a workflow template should be changed from the "generic" workflow template to this "specialized" workflow template for further review.

According to one embodiment, the target user may prompt the program 110 to return to the "generic" template, or vice versa, at any time during an interaction with the dataset. As a result, the invention enables target users to transition from generic workflow template to specialized workflow templates. Furthermore, the invention enables target end-users to utilize existing templates of other users, based on specific patient and context-specific variables.

According to one embodiment, workflow templates may offer the individual end user the ability to "turn on" and turn off" the workflow template functionality. According to one embodiment, the end user may switch from a generic workflow template protocol to a specialized workflow template protocol within the same image review electronic workflow system, and the program 110 will comply accordingly.

In one example, a radiologist may review a chest CT using the generic workflow template protocol and may identify a pulmonary nodule, which the radiologist may highlight using the programmable stylus 104, for example. According to one embodiment, the radiologist may instruct the client computer 101 or server 120 to convert the generic chest CT workflow template into a specialized "nodule" workflow template, as described below.

According to one embodiment, the conversion may activate a sequence of events, specific to the radiologic finding (i.e., nodule) in question. According to one embodiment, the radiologist may review the CT dataset using a generic workflow template protocol, which may specify a number of parameters including the imaging plane, slice thickness, processing parameters, navigation speed, window/level presets, and/or other parameters. According to one embodiment, the radiologist may identify a nodule on a specific image and highlight that nodule. The nodule may be highlighted using an input device, such as a mouse, a track ball, an electronic stylus, a speech command, or other input device.

According to one embodiment, the radiologist may issue a command to activate the specialized lung nodule workflow template after highlighting the image and specific finding in question. According to one embodiment, the nodule workflow template protocol may be launched by the program 110, which includes a pre-defined sequence of events, including linear and volumetric measurements of the suspected nodule; calculation of interval change with historical comparison images, such as identifying the same anatomic region in 3-dimensional space; automated density measurement calculation; implementation of decision support tools for nodule characterization, such as textual analysis, computer-aided detection, imaging databases for pattern recognition; query of clinical data to identify risk factors and pertinent medical history; determination of malignant probability based on calculation of doubling time, morphologic characteristics, density, and clinical historical data; among other factors. According to one embodiment, specialized workflow templates may be engaged by the end-user for any pertinent findings. Once the analysis has been completed, the end-user may return to the generic workflow template.

According to one embodiment, the dynamic nature of workflow templates provides unique educational and research applications. From an education standpoint, the entire workflow process may be reviewed and refined retrospectively to identify "best practice" standards and teach different user groups. These user groups may include technologists, residents in training, clinicians, and attending radiologists. Each different user group may have their own customized versions of workflow templates for educational purposes. For example, the technologist educational workflow template may have detailed protocols for image processing and manipulation.

According to one embodiment, the technologist workflow template may audit interactions between technologists and the computer workstations (e.g., CT). According to one embodiment, the simulations may be used for additional technologist training. As these simulated sequences are reviewed, the program 110 may have an electronic wizard pop up on the display, to offer instruction and additional options to the technologist in training.

According to another embodiment, the resident workflow templates may contain detailed protocols for image display, navigation, and interpretation. According to one embodiment, attending radiologists may have educational workflow templates that focus on more esoteric applications of decision support and different reporting strategies. According to one embodiment, clinician workflow templates may focus on clinical data extraction, image review, and supporting data.

According to one embodiment, the research applications of workflow templates may go beyond existing imaging data repositories. According to one embodiment, imaging teaching files, used for both educational and research purposes, may be static in nature and may include collections of images with specific findings and diagnoses. According to one embodiment, the researcher may access the full complement of imaging and clinical data using the workflow templates. According to one embodiment, the researcher may review the entire image review, display, interpretation, and reporting process, along with supplemental data. This provides far more robust data to the researcher and provides the ability to perform outcomes analysis, which is currently constrained by excessive time constraints inherent to chart review, in order to obtain correlating clinical data.

According to one embodiment, a researcher may go through the following sequence of events when searching imaging databases, with and without using an electronic workflow template. For example, a researcher may perform an analysis of patients with metastatic small cell carcinoma. The researcher may desire to evaluate a number of different factors including patient demographic profiles; the extent of disease at time of diagnosis; response to treatment; imaging characteristics of disease (before, during, and after treatment); anatomic locations of disease; and diagnostic accuracy of different imaging modalities, among other factors.

In the current research environment, the researcher would access available imaging databases and search under the diagnosis of metastatic small cell carcinoma. The researcher would find large numbers of annotated images of different anatomic locations and different imaging modalities, with a minimum of supporting clinical data.

According to one embodiment of the invention, the researcher may access the workflow template capabilities to access to the full complement of clinical (i.e., EMR) and imaging data (i.e., PACS) that is contained within the comprehensive workflow template. In addition to the ability to review the entire imaging dataset, the electronic consultative capabilities of the electronic workflow template also provides a time stamped record of additional data inputs, queries, and clinical outcomes, that may be automatically queried and retrieved using computerized intelligent agents of the program 110.

According to one embodiment, data contained within the workflow template may be represented in a non-proprietary, standardized format, which is independent of individual vendors PACS and EMR technologies, using DICOM-SR standards. This allows for workflow templates that are archived from different facilities to contain easily accessible and anonymized data, in a standardized format.

According to one embodiment, short cuts may be incorporated into the electronic workflow system process. According to one embodiment, the short cuts may be independent of the end user and the client computer 101 or server 120 that are accessed for review. According to one embodiment, the short cuts may be incorporated into the computer keyboard (e.g., Control S equals "Start, Control P equals "Stop", etc.), a programmable mouse, delivered via speech commands, and/or provided via other devices.

According to one embodiment, if a clinician desires to skip a portion of the electronic workflow system, the clinician may select the "Skip" command manually, via speech and/or through another method. According to one embodiment, the present invention may provide enhanced functionality as compared to a DVD remote control. As discussed above, the present invention may enable users to perform functions on the electronic workflow system, such as rewinding, skipping, fast forwarding, and/or other performed functions.

According to one embodiment, end-users may elect to store the XML code for "edited" electronic workflow systems as a standard default for future review. According to one embodiment, when the clinician accesses a selected electronic workflow system at a future date, the "recently edited" electronic workflow system may be presented as the default electronic workflow system. According to one embodiment, the amended XML schema may direct play back of the imaging data, based on the revisions made during a previous electronic workflow system.

According to one embodiment, a report or other document may be associated with an electronic workflow system having an XML format. According to one embodiment, the report or other document may include a conventional text based document. According to another embodiment, the report or other document may include a DICOM structured report, which may be accessed automatically or may be accessed by activating a specific icon, such as a movie camera.

According to one embodiment, end users may access the structured reporting icon at any time to reconfigure a customized workflow template. According to one embodiment, the workflow template may be context-specific. According to another embodiment, the workflow template may be based on a specific imaging modality, anatomy being reviewed, a specific type of pathology, and/or other factors. According to one embodiment, embedded links may be incorporated into the electronic workflow system by the program 110 to provide access to decision support tools, web sites (via specific URL's), and/or other resources. According to one embodiment, embedded links may supplement the informational content being shared.

By contrast, while a number of decision support tools may be currently available, decision support tools may not be accessed on a routine basis in current medical interpretation processes. One example of a decision support tool is computer-aided detection software (CAD), which has a number of existing applications such as applications to lung nodules, colonic polyps, breast calcifications, and pulmonary emboli. Another example of a decision support tool is segmentation, which allows for individual components within an image to be segmented, such that different organ systems may be isolated.

According to one embodiment, the program 110 of the present invention may embed decision support tools into the present electronic workflow system. In one example, a patient may undergo a chest CT after presenting with a cough and suspected lung cancer. According to one embodiment, a pulmonologist reviewing the electronic workflow system may access and incorporate a CAD program to automate lung nodule detection. According to one embodiment, the CAD program 110 may include a pre-determined CAD overlay, which is based on the specific pulmonologist's preferences.

According to one embodiment, the pulmonologist concurrently may desire to have segmentation incorporated into the chest CT for detailed assessment of the pulmonary arteries. According to one embodiment, web links may be incorporated into the electronic workflow process by the program 110. According to one embodiment, specific URL's may be included in the XML code by the program 110.

According to one embodiment, the pulmonologist may desire to review recent articles outlining new treatment options for small cell lung carcinoma. Thus, the pulmonologist may embed the URL for an Internet resource, such as the National Library of Medicine, into the electronic workflow system by providing search terms using data entry techniques such as manual entry, speech entry and/or other types of data entry. According to one embodiment, the program 110 of the present invention may provide access to articles that are specific to the search. According to one embodiment, the retrieved articles may be stored for review by the program 110 during the electronic workflow process.

According to one embodiment, the electronic workflow system may incorporate the equivalent of video clips into the EMR, which may become a part of or be independent from the report. According to one embodiment, the electronic workflow system may include other pertinent patient data, such as laboratory data, text notes, pathology, EKG and/or other pertinent patent data so as to create a condensed composite of all data. According to one embodiment, the program 110 of the workflow template system creates a comprehensive shorthand version of key imaging findings by capturing the navigational steps, image presentation states, measurements, and annotations. According to one embodiment, the present invention provides an easy to use vehicle for education and research, by the program 110 storing electronic workflow systems that may be indexed according to various parameters including pathology, organ system, and imaging modality.

According to one embodiment, electronic auditing of clinicians may be performed by the program 110 to identify the specific data that is most commonly accessed and used by clinicians. According to one embodiment, frequently accessed decision support tools may be automatically inserted into the electronic workflow system by the program. According to one embodiment, infrequently accessed decision support tools may be automatically deleted from the electronic workflow system by the program 110. According to one embodiment, an intelligent electronic workflow system may be created that is customized to particular user viewing habits.

According to one embodiment, the XML schema enables the underlying software program 110 employed in the present invention to be open and non-proprietary. According to one embodiment, the program 110 of the present invention facilitates transfer of the electronic workflow system across all picture archival and communication (PAC) systems, irrespective of the vendor. According to one embodiment, the XML schema may be used across multiple devices for image review, including tablet PCs, PDAs, and other wireless devices. According to one embodiment, the auditing tools of the present program 110 may record specific events that occur during a "live" electronic workflow system. According to one embodiment, the auditing tools of the program 110 may record specific events that occur during asynchronous image review and manipulation of data.

According to one embodiment, the present invention provides a bidirectional electronic workflow system. According to one embodiment, the present invention provides improved communication between parties, with the potential to be used as an educational tool as well as a clinical tool to improve diagnostic accuracy and productivity. According to one embodiment, the auditing tool and XML schema may be employed in medico-legal protection by demonstrating what imaging information was reviewed. According to one embodiment, the auditing tool and XML schema may be employed in medico-legal protection to reconstruct the manner in which imaging information was reviewed.

According to one embodiment, the data recorded by the auditing function of the program 110 may verify what portions of the comprehensive dataset were reviewed, what types of image processing was used, what decision support tools were used in the image review/interpretation process, among other auditing information. According to one embodiment, the XML schema may serve as an adjunct to the formal report and may provide the electronic workflow system by recording the image review process. According to one embodiment, the present invention provides an effective electronic communication tool.

According to one embodiment, by storing the workflow templates in XML schema, complex and data-intensive information may be easily accessible and transportable by the program 110. This allows for workflow templates to be modified according to end-user preferences and electronically downloaded. If, for example, a radiologist decides to employ the workflow templates of another radiologist, the radiologist may simply copy the workflow templates and integrate them into his/her customized profile. This action may be performed in a manner that is similar to saving and modifying word processing documents or other known applications. According to one embodiment, files may be created and stored by the program 110 according to anatomic region, imaging modality, clinical indication, pertinent findings, among other factors. By simply saving an added feature, users may direct the program 110 of the workflow template archive to incorporate these modifications into the new workflow templates.

According to one embodiment, if the user manually alters the workflow in any way, the end-user may be prompted by the program 110 to inquire whether the user wants this change to be incorporated into the workflow template (i.e. Save Changes). This provides an easy to use mechanism for adjusting existing workflow template protocols and creating new ones, which can be named by the end user in a context-specific fashion, for future use.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention. The scope of the invention is to be determined solely by the appended claims.

What is claimed is:

1. A method of capturing actions that are performed on at least one medical image of a patient during a medical imaging interpretation, the method being implemented using a computer system, the method comprising:
   (a) displaying a workflow template on a display of the computer system;
   (b) displaying the at least one medical image of the patient on said display;
   (c) automatically extracting data from an electronic medical record of the patient, or other data related to the patient, from a database, into said workflow template provided on said display;
   (d) capturing and storing one or more user actions as they are performed on the medical image of the patient, by an interpreting user during an entire medical imaging interpretation, using an auditing function of the computer system;
   (e) automatically generating user action information from the one or more captured actions, to prompt said user to perform certain actions;
   (f) storing the captured user actions and user action information, along with said data related to the patient, in said database, with the at least one medical image of the patient, as a new workflow sequence onto a new workflow template as a pre-defined protocol;
   (g) accessing said new workflow template having said pre-defined protocol from said database;
   (h) displaying to a new user, in said new workflow template, a recreation of the exact pre-defined protocol including said data related to the patient, stored by said previous interpreting user in said database, as a continuous replica of said previous interpreting user's actions and user action information stored in said workflow sequence, such that said new user may selectively review and modify clinically pertinent medical images and said data related to the patient, in a continuous manner that follows said stored workflow template as created by said previous interpreting user; and
   (i) repeating steps (b)-(f), such that a modified new workflow template is created and stored in said database:
   wherein each said modified new workflow template is a cumulative, refined, and dynamic workflow sequence of a series of said captured user actions and user action information, along with data related to each patient, with the at least one medical image of said patient, in order to provide best practice of said medical image interpretation for said user.

2. The method according to claim 1, further comprising:
applying an extensible markup language schema to perform image data extraction for displaying the medical image, navigating multiple medical images, processing the multiple medical images, applying support tools, or creating reports.

3. The method according to claim 1, wherein the one or more user actions include the computer-implemented assignment of corresponding non-verbal, graphical symbols that are pre-selected to have a defined language meaning.

4. The method according to claim 1, wherein capturing one or more user actions include capturing individual steps that a user performs during said entire medical image interpretation.

5. The method according to claim 1, further comprising presenting the workflow sequence, including medical image review, analysis or interpretation, in a chronological order based on actions performed by a user to create the workflow sequence.

6. The method according to claim 5, further comprising:
enabling manipulation of the workflow sequence;
wherein enabling manipulation of the workflow sequence includes enabling at least one of skipping, fast forwarding or rewinding the workflow sequence.

7. The method according to claim 1, further comprising enabling access to embedded links that are incorporated in the workflow sequence.

8. The method according to claim 7, further comprising:
providing access to support tools or web sites; and
automatically inserting or deleting support tools or web sites from the workflow sequence using the computer system, based on at least one of user actions or frequency of use.

9. The method according to claim 1, wherein a predetermined workflow sequence is automatically executed by the computer system when a specific medical image interpretation is initiated by said new interpreting user.

10. The method according to claim 1, further comprising:
enabling navigation of the workflow sequence in at least one of a computer system-implemented automatic or manual mode.

11. The method according to claim 1, wherein said workflow template is defined according to at least one of data sets or target user groups; and enabling sharing of the workflow template with one or more users.

12. The method according to claim 11, further comprising:
enabling generation of a plurality of workflow templates; and
presenting the plurality of workflow templates for one of user selection or default selection.

13. The method according to claim 1, wherein displaying the medical image includes displaying one of an analog or a digital image.

14. The method according to claim 1, further comprising generating a computer-implemented report based on information derived from the workflow sequence.

15. The method according to claim 11, further comprising enabling editing of the workflow sequence; and enabling at least one of reviewing, editing or modifying of the workflow template.

16. The method according to claim 1, further comprising:
performing an automated audit of user actions during the workflow sequence; and
notifying a user when pre-defined user actions are omitted from the workflow sequence.

17. The method according to claim 1, further comprising automatically performing, using the computer system, selected user actions, including repetitive actions based on anatomy, clinical indications or a patient profile.

18. The method according to claim 1, further comprising applying pre-selected extensible markup language codes to associate data sets with at least one target user;
wherein the at least one target user includes at least one of a radiologist, a family practitioner, an oncologist, a neurosurgeon, a surgeon, a radiation oncologist, a pulmonologist, an orthopedic surgeon or a medical sub-specialist.

19. The method according to claim 1, further comprising electronically tagging user action information to identify at least one of an author, a date or a source of the user action information.

20. The method according to claim 1, further comprising enabling creation of a rule set to route informational content to a target user based on at least one of user specific information or context-specific information;
wherein the informational content is obtained from at least one of a medical enterprise, including electronic medical records, a picture archiving an communication system, radiological information systems or hospital information systems; and
wherein the target user includes at least one of a radiologist, a family practitioner, an oncologist, a neurosurgeon, a surgeon, a radiation oncologist, a pulmonologist, an orthopedic surgeon or a medical sub-specialist.

21. The method according to claim 11, wherein the workflow templates are automatically selected and launched by the computer system based on the occurrence of a pre-defined sequence of events; and
wherein the workflow templates are selected from among at least one of image display workflows, navigation workflows, image processing workflows, interpretation snapshots, reporting snapshots, communication snapshots, or data extraction snapshots.

22. A system for capturing actions that are performed on at least one medical image of a patient, during a medical imaging interpretation, comprising:
a display which displays the at least one medical image of the patient and a workflow template;
means for automatically extracting data from an electronic medical record of the patient, or other data related to the patient, from said database, into said workflow template provided on said display;
means for capturing and storing one or more user actions as they are performed on the medical image of the patient by an interpreting user during an entire medical imaging interpretation, using an auditing function of the computer system;
means for automatically generating user action information from the one or more captured actions, to prompt said user to perform certain actions;
a database which stores the captured user actions and user action information, along with said data extracted from said electronic medical record of the patient, or other data related to the patient, and provided in a new workflow template, with the at least one medical image of the patient, as a new workflow sequence as a pre-defined protocol of said new workflow template; and
means for accessing said workflow template having said pre-defined protocol; wherein said display displays to a new user, a recreation of the exact pre-defined protocol, including said data related to the patient, stored by said previous interpreting user in said database, as a continuous replica of said previous interpreting user's actions, and user action information stored in said new workflow sequence, such that said new user may selectively review clinically pertinent medical images and data related to the patient in a continuous manner that follows said new workflow template as created by said previous interpreting user;
wherein a revised new workflow template is created and stored in said database after each medical interpretation performed by said user; and
wherein said each said revised new workflow template is a cumulative, dynamic workflow sequence of a series of said captured user actions and user action information, along with data related to each patient, with the at least one medical image of said patient, in order to provide best practice of each said medical image interpretation for said user.

23. The method according to claim 1, wherein a unique identifier is used to allow user access to the workflow templates.

24. The method according to claim 1, wherein at least one of the medical images and/or data from the medical images is determined to be key imaging data, and said key imaging data is stored as an abbreviated data snapshot.

25. The method according to claim 1, wherein said workflow template is a continuous video replica of said previous interpreting user's actions and user action information, and is presented as a workflow movie in real-time.

26. The method according to claim 1, wherein the user is notified of any revisions to said workflow template.

27. The method according to claim 1, wherein said workflow template is one of a generic workflow template or a specialized workflow template.

28. The method according to claim 27, wherein the user can alternate between both said generic workflow template or said specialized workflow template, and said alternate use is determined automatically by the computer system based upon predetermined parameters.

29. The method according to claim 27, wherein said generic workflow template is automatically generated by the computer system when a new interpreting user accesses the workflow template.

30. The method according to claim 27, wherein said generic workflow template is provided in a plurality of options, said options being differentiated by one of user attributes or traits, type of examination, or patient data.

31. The method according to claim 1, wherein said refining of said workflow template in order to identify best practice standards is for educational purposes.

32. The method according to claim 21, wherein the workflow templates include at least one of a video clip, laboratory data, text notes, pathology, or an EKG.

33. The method according to claim 1, further comprising:
receiving a request for assistance from said user, and in response thereof, automatically performing, using the computer system, an estimation of existing workflow templates in said database, in order to make a computer-implemented selection of said existing workflow template for said user.

34. The method according to claim 1, further comprising:
performing an electronic auditing of said workflow sequence in order to compile electronic reporting and provide utility for clinical consultation.

35. A method of capturing actions that are performed on at least one medical image of a patient during a medical imaging interpretation, the method being implemented using a computer system, the method comprising:
(a) displaying a workflow template on a display of the computer system;
(b) displaying the at least one medical image of the patient on said display;
(c) automatically extracting data from an electronic medical record of the patient, or other data related to the patient, from a database, into said workflow template provided on said display;
(d) capturing one or more user actions that are performed on the medical image of the patient, by an interpreting user during an entire medical imaging interpretation;
(e) generating user action information from the one or more captured actions;
(f) storing the captured user actions and user action information, along with said data related to the patient, in said database, with the at least one medical image of the patient, as a new workflow sequence onto a new workflow template as a pre-defined protocol;
(g) accessing said new workflow template having said pre-defined protocol from said database;
(h) displaying to a new user, in said new workflow template, a recreation of the exact pre-defined protocol including said data related to the patient, stored by said previous interpreting user in said database, as a continuous replica of said previous interpreting user's actions and user action information stored in said workflow sequence, such that said new user may selectively review and modify clinically pertinent medical images and said data related to the patient, in a continuous manner that follows said stored workflow template as created by said previous interpreting user; and
(i) repeating steps (b)-(f), such that a modified new workflow template is created and stored in said database;
wherein each said modified new workflow template is a cumulative, refined, and dynamic workflow sequence of a series of said captured user actions and user action information, along with data related to each patient, with the at least one medical image of said patient, in order to provide best practice of said medical image interpretation for said user;
wherein computer intelligent agents search pre-selected support tools, web sites, and databases, in order to automatically create links within said workflow sequence to said pre-selected support tools, web sites, and databases, such that said links are integrated within said modified new workflow template.